(12) United States Patent
Antelman

(10) Patent No.: US 6,228,491 B1
(45) Date of Patent: May 8, 2001

(54) HIGH PERFORMANCE COBALT (II,III) OXIDE ANTIMICROBIAL TEXTILE ARTICLES

(75) Inventor: Marvin S. Antelman, Rehovot (IL)

(73) Assignee: Marantech Holding, LLC, East Providence, RI (US)

( * ) Notice: Subject to any disclaimer, the term of this patent is extended or adjusted under 35 U.S.C. 154(b) by 0 days.

(21) Appl. No.: 09/542,199

(22) Filed: Apr. 4, 2000

(51) Int. Cl.7 ............................. D01F 6/00; D01F 11/12
(52) U.S. Cl. ........................ 428/372; 428/375; 442/123
(58) Field of Search ............................. 428/372, 375; 8/490; 442/123

(56) References Cited

U.S. PATENT DOCUMENTS

| | | | |
|---|---|---|---|
| 2,791,518 | 5/1957 | Stokes et al. | 117/120 |
| 4,410,593 | 10/1983 | Tomibe et al. | 428/389 |
| 5,271,952 | 12/1993 | Liang et al. | 427/2 |
| 5,458,906 | 10/1995 | Liang | 427/2.31 |
| 5,762,650 | * 6/1998 | Ruggiero et al. | 8/490 |

\* cited by examiner

*Primary Examiner*—N. Edwards
(74) *Attorney, Agent, or Firm*—Pennie & Edmonds LLP

(57) ABSTRACT

Fibrous textile articles possessing enhanced antimicrobial properties are prepared by the deposition or interstitial precipitation of cobalt (II, III) oxide ($Co_3O_4$) crystals within the interstices of fibers, yarns and/or fabrics forming such articles.

19 Claims, No Drawings

HIGH PERFORMANCE COBALT (II,III) OXIDE ANTIMICROBIAL TEXTILE ARTICLES

BACKGROUND OF THE INVENTION

1. Field of the Invention

This invention relates to textile articles possessing antimicrobial properties and a method for their preparation.

2. Description of Related Art

Textile articles which have been treated to render such articles microbicidal to microorganisms coming in contact with the article are known in the prior art. Such articles include those made from paper, fibers, woven and non-woven textiles and like fabrics which are designed for use in environments such as hospitals, food processing plants, laboratories and other areas where maintenance of germ-free conditions is essential.

For example, U.S. Pat. No. 2,791,518 discloses a method of imparting microbicidal properties to articles such as textiles by immersing the article in a first aqueous solution containing a water-soluble basic nitrogen compound (ammonia) and a monovalent silver salt soluble in said solution, followed by a second immersion in a second solution containing a second salt capable of ion exchange with the silver salt such that a monovalent silver salt precipitate is formed within the article. The formed silver precipitate is sparingly water soluble and imparts microbicidal properties to the articles so treated.

Similarly, U.S. Pat. No. 5,271,952 discloses a method of treating fibers to render them electrically conductive as well as anti-bacterial comprising immersing the fibers in a bath comprising an aqueous solution of a source of divalent copper ions, a reducing agent, sodium thiosulfate and a source of iodide ions, whereby copper iodide is adsorbed into the fibers. Similar techniques for rendering fibers conductive and/or resistant to bacteria involving the use of copper compounds are disclosed in U.S. Pat. Nos. 4,410,593 and 5,458,906.

One of the main problems associated with the use of monovalent silver compounds such as the halides, phosphates or sulfates in such applications is that they are sensitive to ultra-violet light and are thus prone to discoloration after exposure to sunlight, with a gradual loss of effectiveness of antimicrobial properties. Also, many of these compounds are soluble or slightly soluble in hot water which diminishes the antimicrobial properties after only a few launderings of reusable fabrics containing them.

Another problem with respect to the use of copper compounds as interstitially precipitated antimicrobials such as described in the above U.S. Pat. Nos. 5,271,952 and 5,458,906 is that these processes do not readily lend themselves to inclusion in textile production lines. Textile finishing lines involve processes which take minutes and cannot readily accommodate precipitations which require lengthy immersion times of sixty minutes or more.

The main object of the invention is to provide a method of treating fibers and/or configurated textile products so that anti-microbial properties are imparted to them. Another object of the invention is to incorporate into said fibers and textile products a powerful anti-microbial based on an electron active molecular crystal analogous to the molecular crystal, tetrasilver tetroxide, which has been proven one of the most powerful disinfectants known to man.

Another object of the invention is to form a multivalent cobal oxide by interstitial precipitation.

Still another object of the invention is to enable rapid mass production of anti-microbial fibers and textile products.

SUMMARY OF THE INVENTION

The invention provides a fibrous textile article containing a cobalt (II, III) oxide as an antimicrobial agent interstitially deposited within said article, said agent present in said article in an amount sufficient to impart antimicrobial properties to said article.

The invention also provides a process for imparting antimicrobial properties to a fibrous textile article comprising:

a. providing a solution containing divalent cobalt cations;

b. contacting said article with said solution for a period of time sufficient to uniformly wet said article with said solution;

c. immersing said wetted article in a bath containing a second aqueous solution containing a strong alkali and a water soluable per-acid salt oxidizer for a period of time sufficient to interstitially precipitate cobalt (II, III) oxide within said article; and d. removing said article from said bath.

Textile articles prepared in accordance with this invention, particularly woven and non-woven fabrics, exhibit outstanding antimicrobial resistance with respect to pathogens such as bacteria, viruses, yeast and algae, are resistant to degradation upon exposure to sunlight (ultraviolet light) and maintain their excellent antimicrobial properties even after a number of launderings.

DETAILED DESCRIPTION OF THE INVENTION

Imparting anti-microbial (anti-pathogenic) properties to fiber and its derived textile products is achieved in the instant invention by interstitial precipitation of a molecular crystal compound multivalent cobalt oxide such as cobalt (II, III) oxide. Said cobalt moiety is based on concepts derived by analogy from silver (I, III) oxide which is the subject of patents by the instant inventor, e.g., U.S. Pat. No. 5,336,499. That patent describes the antipathogenic properties of silver oxide whose formula $Ag_4O_4$ and mechanism of operation as a molecular device, based on a unique crystal having two monovalent silver (Ag I) ions and two trivalent silver (Ag III) ions in the molecule, have been fully described in said patent, as well as the mechanism of killing pathogens described therein being based on the differential silver electronic activity between Ag(I) and Ag(III), resulting in. electrocution of pathogens followed by binding chelation of pathogenic surfaces. By extrapolating these elucidated concepts, the instant inventor found that cobalt (II, III) oxide ($Co_3O_4$) was capable of killing pathogens in a like manner.

An antimicrobial spectrum of $Ag_4O_4$ is to be found in a published article written by the instant inventor in the annual R&D issue of *Soap Cosmetics Chemical Specialties* 1994, 70, 3 p. 52–59 entitled "Silver (II, III) Disinfectants", shown in Table 1. The spectrum is based on specifications of the Association of Official Analytical Chemists (AOAC).

TABLE 1

Antimicrobial Spectrum of $Ag_4O_4$

| MICROORGANISM | MIC* (PPM) |
|---|---|
| Gram Negatives | |
| *Escherichia coli* 10231 | 2.50 |
| *Escherichia coli* 25254 | 2.50 |
| *Enterobacter cloacae* 13047 | 2.50 |
| *Pseudomonas aeruginosa* 9027 | 1.25–2.50 |
| Gram positives | |
| *Bacillus subtilis* 6633 | 5.00 |
| *Micrococcus lutena* 9341 | 1.25–2.50 |
| *Staphylococcus aureus* 0927 | 2.50–5.00 |
| *Staphylococcus aureus* 27543 | 5.00 |
| *Staphylococcus epidermidis* 12228 | 0.625 |
| *Streptococcus agalactiae* 27956 | 1.25–5.00 |
| *Streptococcus faecium* 10541 | 5.00 |
| *Streptococcus-pyogenes* 7958 | 2.50 |
| Yeast and Mold | |
| *Candida albicans* 16404 | 2.50–5.0 |
| *Saccharomyces cerevisiae* 2601 | 1.25 |

*MIC = Minimal Inhibitory Concentration.

The term "fibrous textile article" as used herein is intended to encompass a wide variety of materials including paper, natural or synthetic fibers, threads and yarns made from materials such as cotton, rayon, wool, jute, nylon, polyesters, polyacetates, polyacrylics as well as cellulosics in general. More particularly, the term refers to fibers woven into a fabric such as knitting, and non-woven fabrics or webbing used in anti-pathogenic applications such as in the medical field, hospitals, biotechnology and food and dairy processing. Exemplary textile products of this genre include bandages, gauze, bandage pads, skin patches, work clothes (both disposable and reusable), bed sheets, masks, dust cloths, safety belts, surgical gowns, ambulance blankets, stretchers, filter materials, diapers, underwear, pajamas, video display terminal screens and the like.

For some antimicrobial applications, $Co_3O_4$ crystals may be deposited within the interstices of fibrous articles by simply soaking the article in an aqueous dispersion of the crystals (dimension of less than 100 Angstroms), or by combining the crystals with a pharmaceutically acceptable carrier medium and applying this composition to the fibrous article. This method of physical incorporation of the crystals is useful where the article is composed of low density or loosely associated fibers such as bandage pads, gauze pads and loosely non-woven products, and particularly laminated products wherein the treated fibrous article is subsequently sandwiched between layers which tend to keep the crystals trapped in the fibrous article. Also, antimicrobial paper products may be made by simply mixing an aqueous dispersion of the $Co_3O_4$ crystals with paper pulp prior to calendaring the pulp.

However, physical incorporation of the crystals is less effective where the treated article is a fiber or yarn or a higher density woven or non-woven fabric, since the preformed crystals cannot sufficiently penetrate into the interstices of such articles. In such cases, deposition via interstitial precipitation is preferred.

Interstitial precipitation of $Co_3O_4$ crystals (generally having an average dimension of less than 100 Angstroms) is accomplished by first providing a solution containing a source of divalent cobalt cations. Next the article to be treated, e.g., a fiber, yarn or a woven or non-woven fabric, is thoroughly wetted with this solution such that the article absorbs solution on fiber surfaces as well at one or more of the interstices between fibrils forming the fiber, between fibers forming the yarn or non-woven fabric, or between the weft and warp yarns present in woven fabrics. Wetting may be accomplished by uniformly spraying the article or more preferably by dipping the article in a bath of the cobalt salt solution for a period of time sufficient for the article to absorb the requisite amount of cobalt salt solution. This time may range from about 15–60 seconds, more preferably about 30 seconds.

Next the wetted article is removed from the immersion bath and optionally squeezed to remove excess solution and immersed in a bath containing a second aqueous solution comprising a strong alkali and a water soluble per-acid salt oxidizer for a period of time sufficient to cause reaction leading to the interstitial precipitation of $Co_3O_4$ crystals in the interstices of the fibrous article. Suitable alkalis for this purpose include sodium or potassium hydroxide, with sodium hydroxide most preferred. Suitable oxidizing peracids include alkali metal persulfates. Sodium and more preferably potassium persulfate is the preferred oxidizer. Reactions in the bath may be accomplished at room temperature or by heating at a temperature of up to 95° C. for a period of time sufficient to maximize yield of $Co_3O_4$, generally from about 30 seconds to about 4 minutes, preferably about two minutes, After the reaction is completed, the treated article is removed from the bath and may be washed several times with water to remove soluble inpurities or unreacted reagant.

The quantity of $Co_3O_4$ crystals present in the resulting article will generally be a function of the quantity of cobalt salt sorbed by the article, which can vary depending on the nature of the article, e.g., loose vs. tight weave fabrics or whether the fiber is natural or synthetic, the former being more absorbtive of the cobalt salt solution.

In general, the quantity of alkali present in the second bath should be sufficient to maintain a pH on the basic side, i.e., above about 9. The content of $Co_3O_4$ crystals interstitially precipitated within any given fibrous article may be controlled by varying the concentration of the cobalt salt in the solution used to first wet the article.

The antimicrobial properties of the articles treated in this invention may be further enhanced by including a source of fluoride ions in the second oxidizing bath described above. Such sources include water soluble fluoride salts such as sodium or potassium fluoride. The amount of fluoride anion source may generally range from about 10 to 1500 mg per liter of solution, more preferably from about 100 to 1000 mg/liter.

The content of the $Co_3O_4$ (based on weight PPM cobalt) in the fabric may range from as little as 0.5 weight PPM up to about 15,000 weight PPM, based on the weight of the textile article. The minimum content should be sufficient to kill pathogens from which protection is sought, whereas the maximum content is dictated by factors such as economy and affect on fabric properties. Generally speaking, the higher the cobalt content, the more effective will be the antimicrobial properties of the fabric. For most applications, cobalt content in the range of from about 1000 to about 15,000 weight PPM will provide satisfactory antimicrobial properties.

Antimicrobial properties are evaluated in accordance with this invention using the Association of Official Analytical Chemists (AOAC) test method 972.04, which is used primarily to evaluate the bacteriostatic activity of laundry additive disinfectants. In this test, a square sterile swatch of fabric is pressed into a petri dish containing a layer of nutrient agar which has been inoculated with a pathogen. Following a fixed period of incubation, each fabric sample is evaluated by measuring the clear zones adjacent the four sides of each test swatch as an index of antimicrobial activity. The presence of clear zones along all four sides of the swatch is indicative of antimicrobial activity, rated 4/4. The width of the clear zones in millimeters is reasonably indicative of the degree of antimicrobial activity.

In the following examples, assorted fibers and textile swatches were dipped for different periods of time into cobalt chloride solutions of varying concentrations. The take-up of cobalt ions was determined by gravimetric means on an analytical balance, so that for each fiber and textile swatch so treated the exact amount of cobalt in PPM was known. Said fibers were then dipped into an aqueous mixture of sodium hydroxide and potassium persulfate for various periods of time. The sequential treatment was designed to fort $Co_3O_4$ via the mechanism of interstitial precipitation in the fibers and fiber components of the textiles utilized according to the equation:

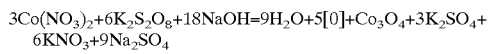

$$3Co(NO_3)_2 + 6K_2S_2O_8 + 18NaOH = 9H_2O + 5[O] + Co_3O_4 + 3K_2SO_4 + 6KNO_3 + 9Na_2SO_4$$

The fibers comprising the materials utilized in the anti-pathogenic treatments were of polyester and nylon. Of the fabrics tested, both predyed goods and undyed virgin materials were evaluated. The AOAC anti-pathogenic tests on said fibers and textiles were performed by an independent laboratory which was licensed by a State environmental regulatory body. The marker organisms used in conformity with AOAC test method 972.04 were *Pseudemonas aeruginosa* (pa) as the Gram negative bacteria marker, and Staphylococcus aureus (Staph) for Gram positive bacteria.

The tests were conducted in terms of inhibition of cultures of said bacteria. Swatches were used for the tests in contact with the cultures. Each swatch had four sides and two swatches were used with each representative culture so that a total of eight trials were reflected with each bacterium. An 8/8 inhibition would indicate 100% efficacy. However, the test protocol went beyond the specifications of the AOAC methods insofar that the actual average inhibition zone in millimeters was recorded for both swatches tested. Accordingly, 8/8 positive results were obtained with the marker bacteria cultures. These results were then combined with the aforementioned anti-microbial spectrum shown in Table 1 which includes the marker bacteria of the AOAC tests, and extrapolated. The conclusion was that the preferred embodiments of the instant invention were 100% effective against the listed Table 1 microbes.

The following examples are illustrative of the invention.

EXAMPLE 1

A swatch of virgin nylon webbing of a standard size, 2.0×5.0 millimeters, was taken and immersed in a cobalt chloride solution containing 10,850 PPM of cobalt for 30 seconds. A gravimetric determination of the cobalt absorbed after immersion showed Co at 9,363 PPM in the webbing. The webbing was then immersed in a room temperature solution containing 50.0 grams/liter potassium persulfate and 22.5 grams/liter sodium hydroxide for two minutes. It was removed, washed and dried. There resulted a dark brown coating on the fibers. The swatch was divided in thirds to give three swatches, two for testing in compliance with the aforementioned AOAC bacterial test 972.04. Zones of inhibition were obtained on all eight sides, i.e., 8/8, for both marker organisms. The average inhibition zones were 1.0 mm for *pseudomonas aeruginosa* and 1.1 for *Staph aureus*.

EXAMPLE 2

Example 1 was repeated in all aspects excepting that the solution chemistries were changed and immersion time in oxidizer was reduced to one minute. Cobalt as chloride was 5,400 PPM. Co on fabric was 4,222 PPM. The oxidizer persulfate was identical to Example 1 excepting that 600 mg per liter of sodium fluoride were added. The results for the Staph marker bacteria were 8/8. The average inhibition zones was 2.0 mm. The addition of fluoride enhanced the efficacy of the fibers against Staph as seen in the inhibition zone being higher than in Example 1 with only 45% of the cobalt concentration that was effective in Example 1.

EXAMPLE 3

An independent medical researcher in Israel obtained a very virulent strain of Staph from a patient at the Shaarei Tzedek Hospital in Jerusalem. The patient subsequently died from the infection. This strain was evaluated as more virulent than any of the other Staph micro-organisms listed in Table 1 by the pathology staff at the Jerusalem hospital. This Staph strain was utilized as the Staph source by the researcher who performed the aforementioned AOAC test 972.04 for bacterial retardation efficacy on the third swatch set aside in Example 1. Since there was only one swatch, there were only four sides to be reckoned with. The virulent strain of Staph was inhibited 100% giving a reading of 4/4. The average inhibition for the 4/4 result was 1.5 mm. Since the virulent strain of Staph qualified on a silver (I, III) oxide scale as having an MIC of 30.5–61 PPM, the values were extrapolated for all Gram positive bacteria listed in Table 1. It was concluded that precipitated Co (II, III) oxide was capable of inhibiting all of the listed Gram positive bacteria. By applying the same reasoning to the Gram negative microorganisms of Example 1 pa marker, one can claim inhibition as well for all Gram negative bacteria listed in Table 1.

Fabrics treated in accordance with this invention hold promise for many antimicrobial applications ranging from preventing jock itch when applied to athletic supporters to preventing scabies and bed sores with treated bed sheets or hospital gowns used in nursing homes and hospitals.

What is claimed is:

1. A fibrous textile article comprising a cobalt (II, III) oxide as an antimicrobial agent interstitially deposited within said article, said agent present in said article in an amount sufficient to impart antimicrobial properties to said article.

2. The article of claim 1 wherein said agent is interstitially deposited by interstitial precipitation.

3. The article of claim 2, wherein said textile article includes woven or non-woven fabric.

4. The article of claim 3 wherein said agent is present within said fabric at a level in the range of about 0.5 to about 15,000 weight PPM, based on the weight of cobalt.

5. The article of claim 2 wherein said antimicrobial properties are sufficient to yield microbial inhibition zones extending beyond 1 mm of fabric swatch borders as measured by AOAC test 972.04.

6. The article of claim 2, further comprising a plurality of fluoride ions.

7. A textile article comprising cobalt (II, III) oxide interstitially deposited therein in an amount sufficient to impart anti-pathogenic properties to the article.

8. The article of claim 7, further comprising fluoride ions in an amount sufficient to enhance the anti-pathogenic properties of the article.

9. The article of claim 7, wherein the textile article includes woven or non-woven fabric.

10. The article of claim 7, wherein the cobalt oxide is present within the article in an amount of about 0.5 to about 15,000 weight PPM, based on the weight of cobalt.

11. The article of claim 10, wherein the cobalt oxide is present within the article in an amount of about 1000 to about 15,000 PPM.

12. The article of claim 7, wherein the article is at least one of a bandage, gauze, a bandage pad, a skin patch, clothing, a bed sheet, a mask, a dust cloth, a safety belt, a surgical gown, a blanket, a stretcher, a filter, a diaper, or a video display screen.

13. The article of claim 7, wherein the textile article comprises a fiber, thread, or yarn.

14. The article of claim 7, wherein the anti-pathogenic properties comprise at least one of anti-bacterial or anti-viral properties.

15. The article of clam 7, wherein the article is comprised of low density or loosely associated fibers.

16. The article of claim 15, wherein the cobalt oxide is interstitially deposited within the article by physical incorporation.

17. The article of claim 7, wherein said textile article is a paper product.

18. A composite article comprising:

a first layer;

as a second layer, the article of claim 7; and a third layer, wherein the second layer is disposed between the first and third layers so as to facilitate the retention of the cobalt oxide therein.

19. The composite article of claim 18, wherein the article is laminated.

* * * * *